(12) United States Patent
Shah et al.

(10) Patent No.: US 6,462,164 B1
(45) Date of Patent: Oct. 8, 2002

(54) 2-PHENYLIMIDAZOLE-PHOSPHORIC ACID SALT AS AN ACCELERATOR FOR ACID ANHYDRIDE CURATIVES IN ONE-COMPONENT EPOXY COMPOSITIONS

(75) Inventors: Dilipkumar Nandlal Shah, Wescosville, PA (US); William Edward Starner, Nesquehoning, PA (US)

(73) Assignee: Air Products and Chemical, Inc., Allentown, PA (US)

( * ) Notice: Subject to any disclaimer, the term of this patent is extended or adjusted under 35 U.S.C. 154(b) by 84 days.

(21) Appl. No.: 09/703,443

(22) Filed: Nov. 1, 2000

(51) Int. Cl.$^7$ ............................................. C08G 59/68
(52) U.S. Cl. ......................... 528/89; 528/94; 528/112; 548/377.1
(58) Field of Search ........................ 528/89, 94, 112; 548/377.1

(56) References Cited

U.S. PATENT DOCUMENTS

| 3,329,652 A | 7/1967 | Christie ........................ 260/47 |
| 3,356,645 A | 12/1967 | Warren ........................ 260/47 |
| 3,631,150 A | 12/1971 | Green ........................ 260/47 |
| 3,632,427 A | 1/1972 | Green ........................ 117/161 |
| 4,788,076 A | 11/1988 | Weiss ........................ 427/27 |
| 5,508,328 A | 4/1996 | Olson ........................ 523/445 |
| 5,534,565 A | 7/1996 | Zupancic et al. ........... 523/454 |

OTHER PUBLICATIONS

Sawa et al., Abstract of JP 2053777, Feb. 1990.*
Kazushi, Abstract of JP 59020371, Feb. 1984.*
Lee & Neville, Handbook of Epoxy Resins, McGraw–Hill pp. 12–2, 12–12, 1967*
T. Kamon, et al., "Curing of Epoxy Resins," Shikizai Kyokaishi (1977), 50(1), 2–7, Chemical Abstracts 86:172311.
N. Sawa, et al., "Preparation of 1–Benzylimidazoles as Epoxy Resin Hardeners," Japan Kokai Tokkyo Koho, 6 pp., Chemical Abstracts 113:78398.
European Search Report, 01125886.0–21–2, dated Mar. 7, 2002.
European Search Report, 01125885.2–1202, dated Mar. 8, 2002.

* cited by examiner

Primary Examiner—Robert Dawson
Assistant Examiner—D. Aylward
(74) Attorney, Agent, or Firm—Michael Leach

(57) ABSTRACT

A heat curable, a one-component epoxy protective or decorative coating or adhesive composition comprising an epoxy resin, acid anhydride latent heat activated curing agent and an accelerator for the acid anhydride curing agent characterized in that 2-phenylimidazole phosphate salt is the accelerator.

19 Claims, 7 Drawing Sheets

1-MIP

IMP

2-EIP

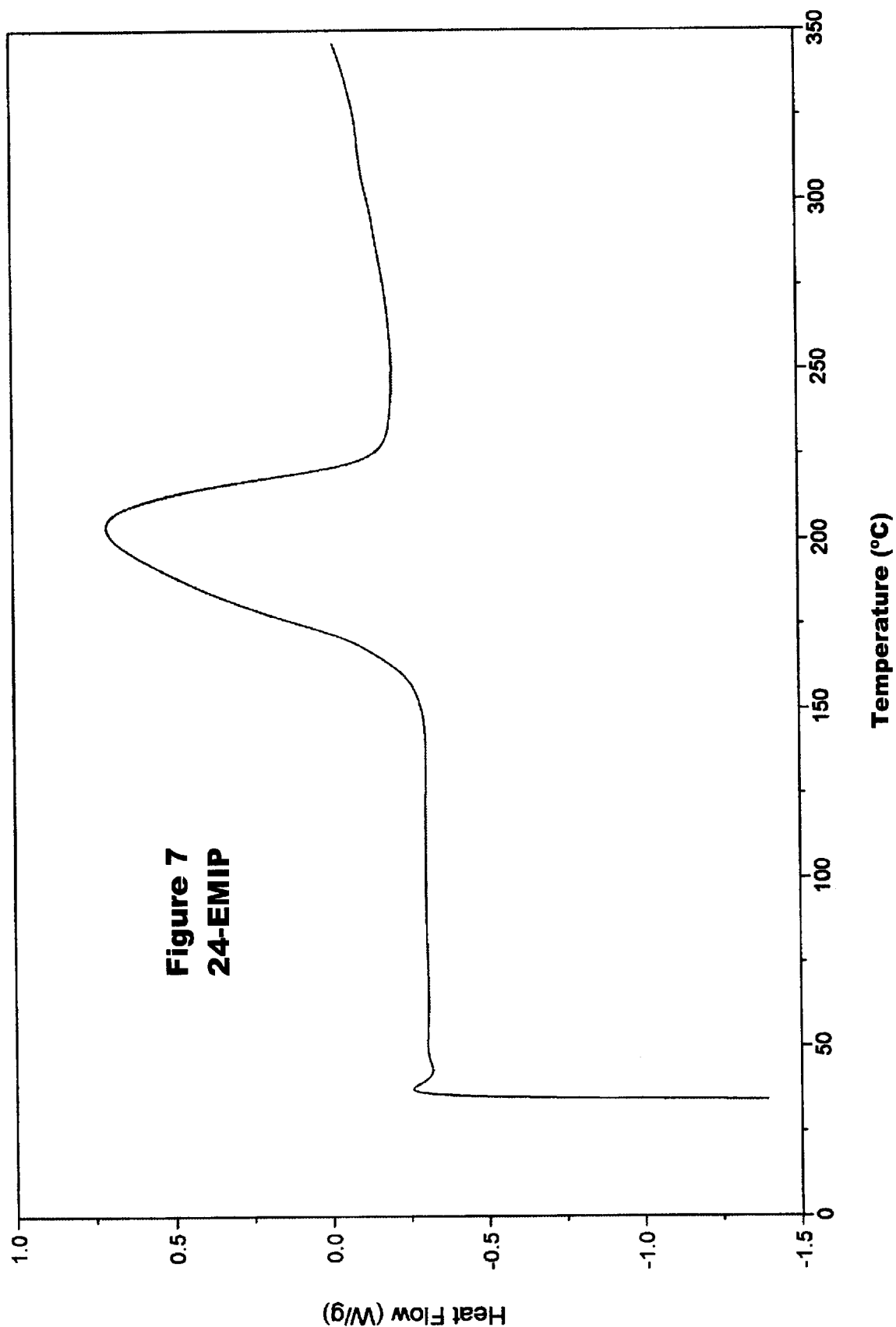

2-PHENYLIMIDAZOLE-PHOSPHORIC ACID SALT AS AN ACCELERATOR FOR ACID ANHYDRIDE CURATIVES IN ONE-COMPONENT EPOXY COMPOSITIONS

BACKGROUND OF THE INVENTION

The present invention relates to latent curing agents and accelerators for epoxy resins, especially one-component epoxy compositions. "Latent" curing agents are those curatives that in a formulated system remain inactive under normal ambient conditions but react readily with epoxy resin at elevated temperatures. "Accelerators" are those materials that accelerate the reaction between epoxy resin and a curing agent. "One component" epoxy compositions are typically a blend of epoxy resin, curing agent and accelerator as well as additives and fillers.

Current one-component epoxy compositions may contain an acid anhydride as a latent curing agent. These compositions offer excellent shelf life but require very high temperature to cure. Accelerators such as imidazoles can be used with acid anhydrides to increase reactivity, however such accelerators adversely affect shelf stability of compositions.

There is a need for a one-component 100% solids epoxy composition which is cured by acid anhydride and offers a good balance of low-temperature cure and shelf stability.

U.S. Pat. No. 3,329,652 discloses curing polyepoxides with acid anhydrides using imidazole salts as activators for the acid anhydride.

U.S. Pat. Nos. 3,356,645 and 3,418,333 disclose curing polyepoxides with imidazole salts.

U.S. Pat. No. 3,746,686 discloses curable epoxy resin compositions comprising a polyepoxide and a salt of a polycarboxylic acid or anhydride and an imidazole.

U.S. Pat. No. 3,755,253 discloses catalyzing the diaminodiphenylsulfone cure of polyepoxides with an imidazole salt.

T. Kamon, et al, "Curing of Epoxy Resins. VI. Curing of Epoxy resins with Acid Salts of Imidazoles", Shikizai Kyokaishi (1977), 50 (1), pp 2–7 discloses the study of the curing of epoxy resins with alkyl carboxylic acid and phosphoric acid salts of some imidazoles.

JP 58083023 describes a latent epoxy hardener prepared by placing 2-hepta-decylimidazoline in water, adding orthophosphoric acid, mixing for 10 minutes, filtering and drying in vacuo. "Epoxy Dispersion In Adhesive Applications", Adhesives Age, May 1995, pages 34–37, discloses the use of 2-methylimidazole and dicyandiamide in water-based epoxy compositions.

SUMMARY OF THE INVENTION

The present invention is directed to 2-phenylimidazole phosphate salt and its use as an accelerator for acid anhydride latent curing agents in one-component heat curable epoxy compositions. The salt is the reaction product of 2-phenylimidazole and phosphoric acid.

The reaction of 2-phenylimidazole with phosphoric acid, especially in equimolar amounts, affords the dihydrogen phosphate salt, or biphosphate salt, of the following structure A

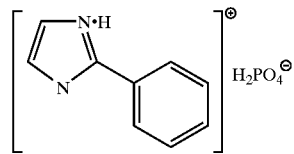

The invention provides:
an accelerator for acid anhydride latent curatives in heat cured epoxy compositions; and
one-component 100% solids epoxy compositions comprising 2-phenylimidazole phosphate salt, acid anhydride and an epoxy resin which offer a good balance of low-temperature cure and extended shelf stability.

BRIEF DESCRIPTION OF THE DRAWINGS

FIG. 7 is the differential scanning calorimetric graph of 2-ethyl-4-methylimidazole phosphate as an accelerator in the anhydride cured epoxy composition of Example 14.

DETAILED DESCRIPTION OF THE INVENTION

Figure 1:
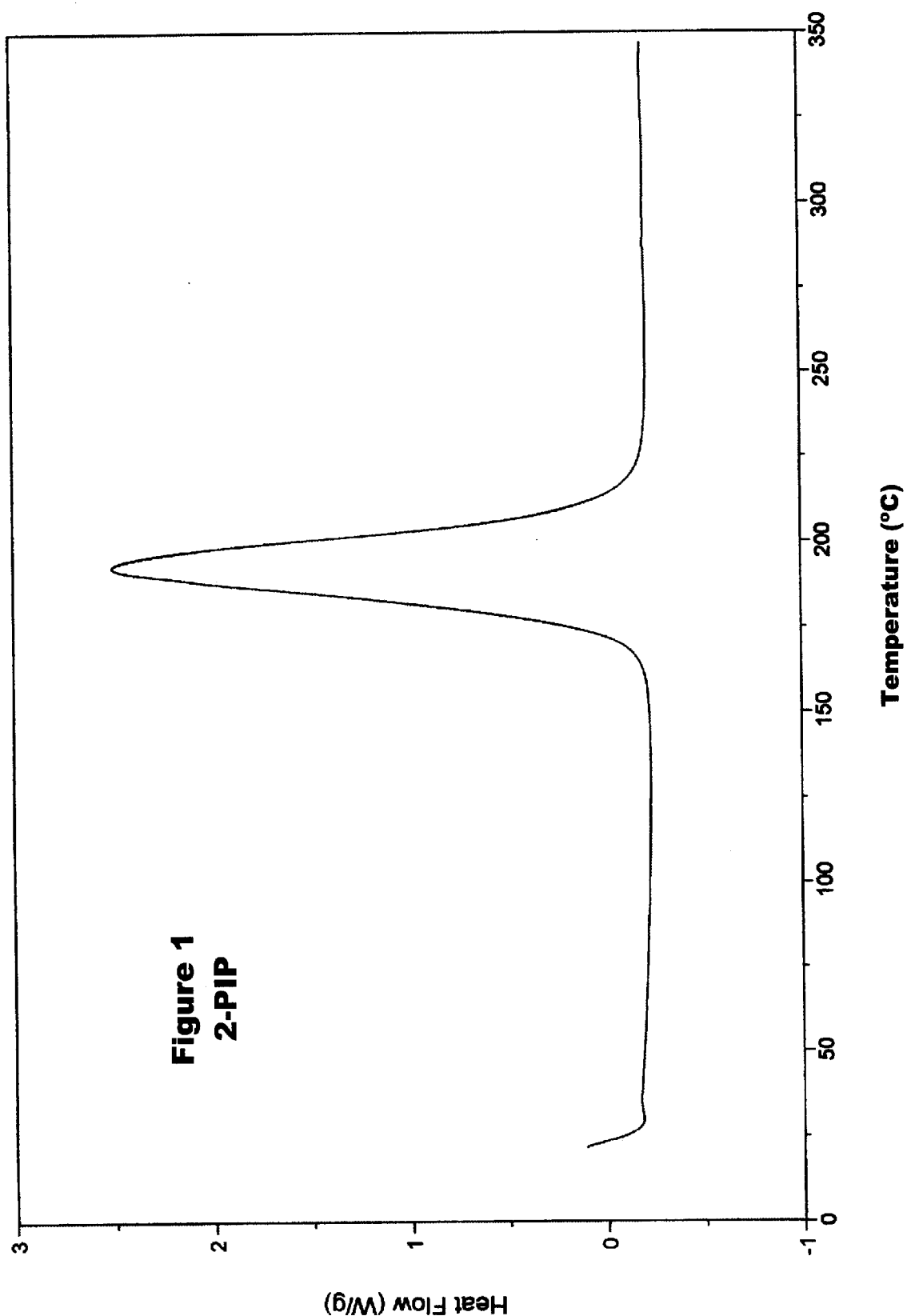
FIG. 1 is the differential scanning calorimetric graph of 2-phenylimidazole phosphate as an accelerator in the anhydride cured epoxy composition of Example 8.

The invention relates to the phosphoric acid salt of 2-phenylimidazole and its use as an accelerator for acid anhydrides in curing epoxy resins. (Phosphoric acid is also known as orthophosphoric acid and is commercially available as 85% phosphoric acid.) The salt having structure A is the monobasic salt formed by the reaction of 1 mole of 2-phenylimidazole with 1 mole of phosphoric acid according to the reaction scheme:

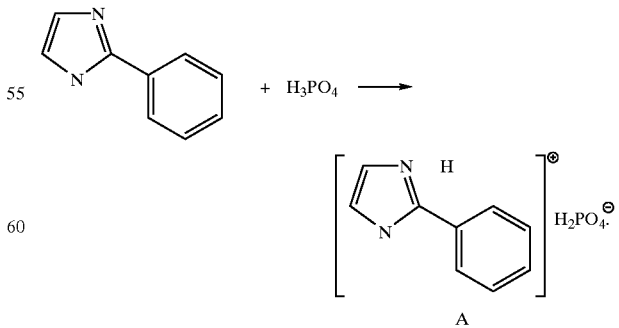

The stoichiometry employed in the synthesis of the phosphate salt can be any combination, e.g., ranging from 0.1 moles to 5.0 moles of 2-phenylimidazole and 0.1 moles to >5.0 moles of phosphoric acid. Generally, the 2-phenylimidazole and the phosphoric acid are reacted in a 0.9 to 1.1 molar ratio, preferably a 0.95 to 1 molar ratio. Typically the commercially available 85% orthophosphoric acid is employed but any concentration can be used in this invention. The reaction can be conducted with or without the use of solvent. The solvents may be but are not limited to water, methanol, ethanol, THF and the like. Any solvent which will dissolve one of the reactants or the product may be used. Any order of addition may be used and the reaction may be conducted at any temperature or pressure desired as they are not critical to making the salt. The preferred method of synthesis is to dissolve the 2-phenylimidazole in methanol and add the orthophosphoric acid slowly to the imidazole solution. The resulting precipitated salt is collected by filtrating, washing with methanol and air drying.

The 2-phenylimidazole/phosphoric acid salt can be used as an accelerator for acid anhydride latent curing agents in one-component epoxy adhesives, decorative and protective coatings including powder coatings, filament winding, printed circuit board and like epoxy applications.

The acid anhydrides suitable for use as the latent epoxy curative in this invention are any of those curative materials known in the epoxy art such as those disclosed at Col 2/28-71 of U.S. Pat. No. 3,329,652, which is incorporated by reference. Preferred anhydrides comprise the aliphatic, cycloaliphatic and aromatic mono- and dianhydrides. Especially preferred are the normally liquid or low melting anhydrides such as Nadic methyl anhydride (methylbicyclo [2,2,1]heptene-2,3-dicarboxylic anhydride isomers), tetrahydrophthalic anhydride, methyltetrahydrophthalic anhydride, hexahydrophthalic anhydride and methylhexahydrophthalic anhydride. Typically, 75 to 90 parts by weight (pbw) acid anhydride are used in the epoxy composition per 100 pbw epoxy resin, preferably 80 to 85 pbw acid anhydride.

The 2-phenylimidazole phosphate accelerator and the acid anhydride latent curing agent are combined with an epoxy resin which is a polyepoxy compound containing more than one 1,2-epoxy groups per molecule. Such epoxides are well known in the epoxy art and are described in Y. Tanaka, "Synthesis and Characteristics of Epoxides", in C. A. May, ed., Epoxy Resins Chemistry and Technology (Marcel Dekker, 1988). Examples include those epoxides disclosed in U.S. Pat. No. 5,599,855 (Col 5/6 to 6/20), which is incorporated by reference. The preferred polyepoxy compounds are the diglycidyl ethers of bisphenol-A, the advanced diglycidyl ethers of bisphenol-A, the diglycidyl ethers of bisphenol-F, and the epoxy novolac resins. Both liquid epoxy resins and solid epoxy resins are suitably used in the one component epoxy compositions. Powder coating compositions would comprise a solid epoxy resin, 2-phenylimidazole phosphate salt and anhydride.

Generally, an effective amount of the 2-phenylimidazole phosphate salt for accelerating the curing of the epoxy resin is used. As an accelerator for an acid anhydride curative, 0.05 to 10 parts by weight (pbw) of the phosphate salt would be used per 100 pbw of epoxy resin.

Compositions prepared from 2-phenylimidazole-phosphoric acid salt, acid anhydride and epoxy resins can be formulated with a wide variety of ingredients well known to those skilled in the art of coating formulation, including solvents, fillers, pigments, pigment dispersing agents, rheology modifiers, thixotropes, flow and leveling aids, defoamers, etc. Epoxy compositions comprising about 1 to 90 wt % organic solvents or 100% solids can be used.

One component epoxy compositions of this invention can be applied as coatings by any number of techniques including spray, brush, roller, paint mitt, and the like. Numerous substrates are suitable for application of coatings of this invention with proper surface preparation, as is well understood in the art. Such substrates include but are not limited to many types of metal, particularly steel and aluminum, as well as concrete.

One component epoxy coating compositions of this invention can be applied and cured at elevated temperatures ranging from about 125° C. to about 240° C., with cure temperatures of 150° C. to 190° C. preferred.

EXAMPLES 1–7

These examples show the preparation of imidazole phosphate salts prepared from the reaction 2-phenylimidazole (2-PI), 1-methylimidazole (1-MI), 2-methylimidazole (2-MI), imidazole (IM), 4-methylimidazole (4-MI), 2-ethylimidazole (2-EI) and 2-ethyl-4-methylimidazo (24-EMI) with 85% phosphoric in 1:1 molar ratio. The procedure used to prepare these imidazole phosphates was as follows:

To a 250 ml round bottom 3-necked flask equipped with a magnetic stirrer, thermocouple, condenser and dropping funnel were added 100 ml of methanol and the appropriate amount of the desired substituted imidazole, e.g., 36.0 g (0.25 mole) of 2-phenylimidazole (2-PI). After the dissolution of the imidazole was complete the 85% phosphoric acid was added dropwise over a 15 minute period. When addition was complete the resulting slurry was mixed for 15 minutes. The solid product was isolated by filtration in a Buchner funnel, washed with 50 ml of fresh methanol and dried in air. The amount of imidazole phosphate salt recovered was 99% of the theoretical yield.

The reactant amounts, imidazole phosphate salt yields, their melting points as determined by differential scanning calorimetry (DSC) and pH of a 5% solution of each preparation are shown in Table 1:

TABLE 1

| Example | Imidazole (g) | 85% $H_3PO_4$ (g) | Imidazole Salt (g) | Melting Point (° C.) | pH of 5% aq soln |
|---|---|---|---|---|---|
| 1 | 36.0 (2-PI) | 28.8 | 56.5 | 245 | 4.9 |
| 2 | 20.5 (1-MI) | 28.8 | 43.9 | 121 | 4.7 |
| 3 | 20.5 (2-MI) | 28.8 | 44.0 | 162 | 5.2 |
| 4 | 17.3 (IM) | 28.8 | 41.5 | 109 | 4.5 |
| 5 | 20.5 (4-MI) | 28.8 | 39.6 | 112 | 4.6 |
| 6 | 24.0 (2-EI) | 28.8 | 41.7 | 144 | 4.8 |
| 7 | 27.5 (24-EMI) | 28.8 | 53.6 | 173 | 4.6 |

EXAMPLES 8–14

These examples of 100% solids epoxy systems demonstrate the imidazole phosphate salts as accelerators for an acid anhydride cured epoxy resin composition. The compositions were prepared by thoroughly mixing the following ingredients:

Epon 828 100.0 g

Methylhexahydrophthalic anhydride 90.0 g

Imidazole phosphate salt 0.5 g

The imidazole phosphate salts were designated as follows:

2-Phenylimidazole phosphate (2-PIP)

1-Methylimidazole phosphate (1-MIP)

2-Methylimidazole phosphate (2-MIP)

Imidazole phosphate (IMP)

4-Methylimidazole phosphate (4-MIP)

2-Ethylimidazole phosphate (2-EIP)

2-Ethyl-4-methylimidazole phosphate (24-EMIP)

Figure 2:
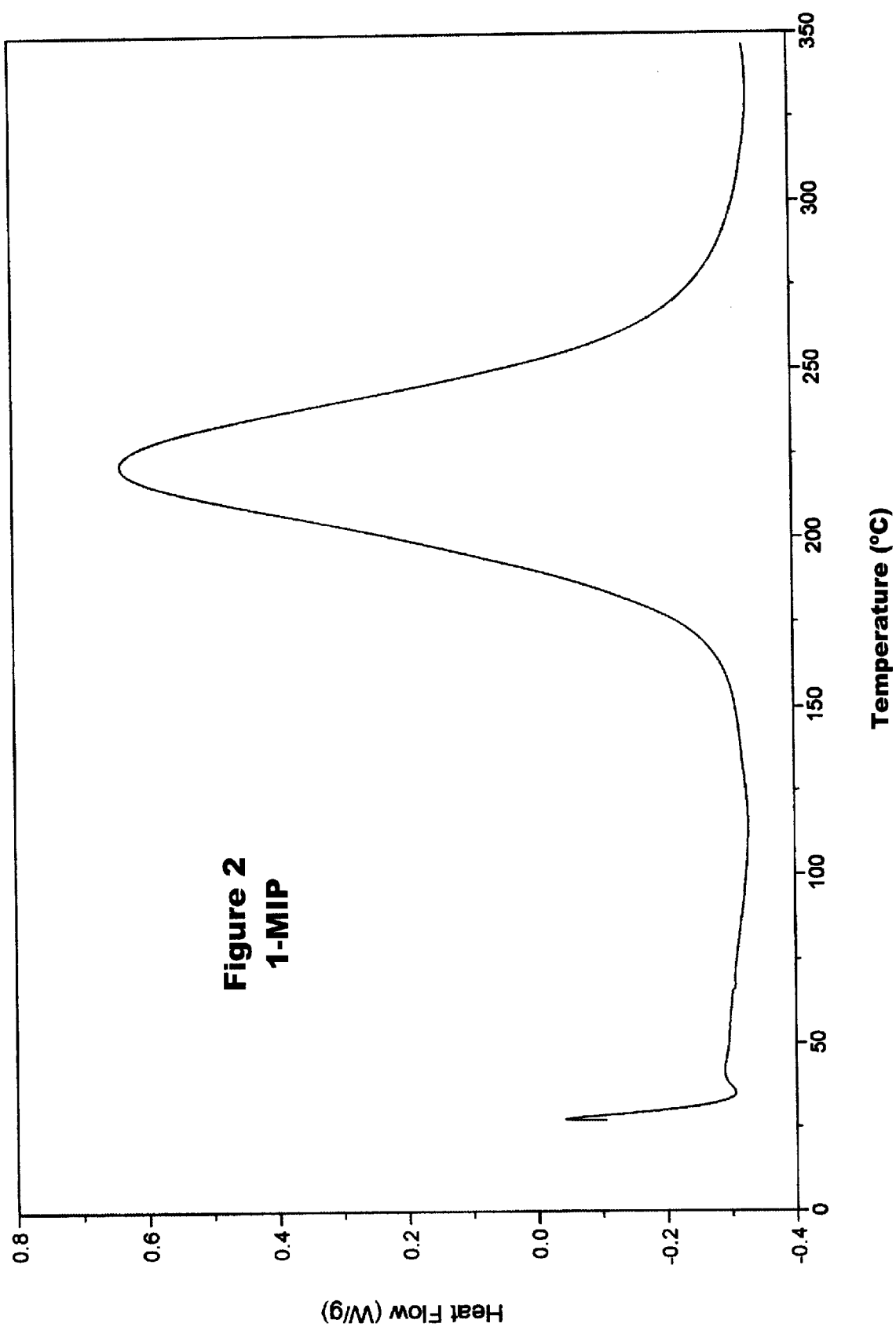
FIG. 2 is the differential scanning calorimetric graph of 1-methylimidazole phosphate as an accelerator in the anhydride cured epoxy composition of Example 9.
Figure 3:
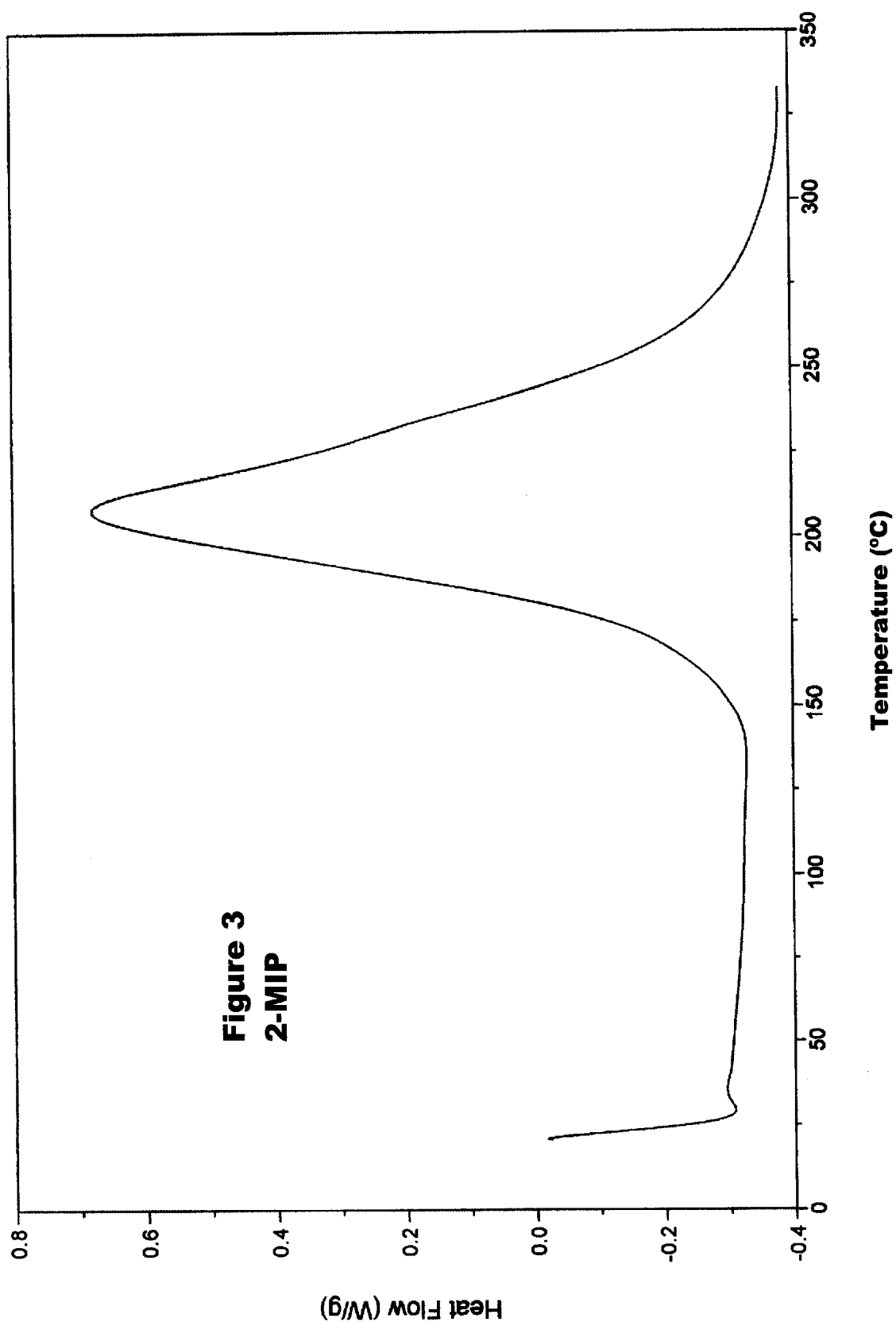
FIG. 3 is the differential scanning calorimetric graph of 2-methylimidazole phosphate as an accelerator in the anhydride cured epoxy composition of Example 10.
Figure 4:
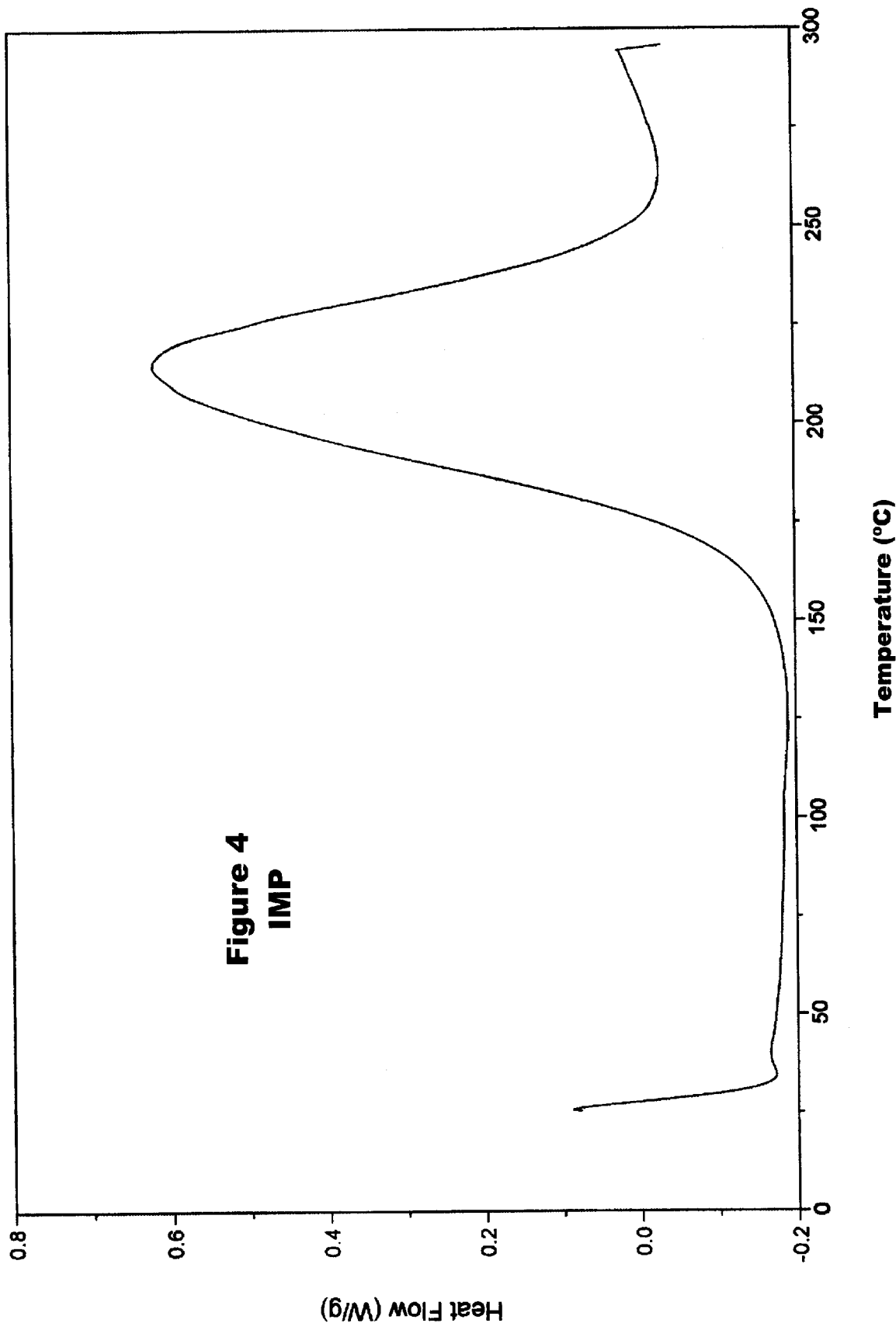
FIG. 4 is the differential scanning calorimetric graph of imidazole phosphate as an accelerator in the anhydride cured epoxy composition of Example 11.
Figure 5:
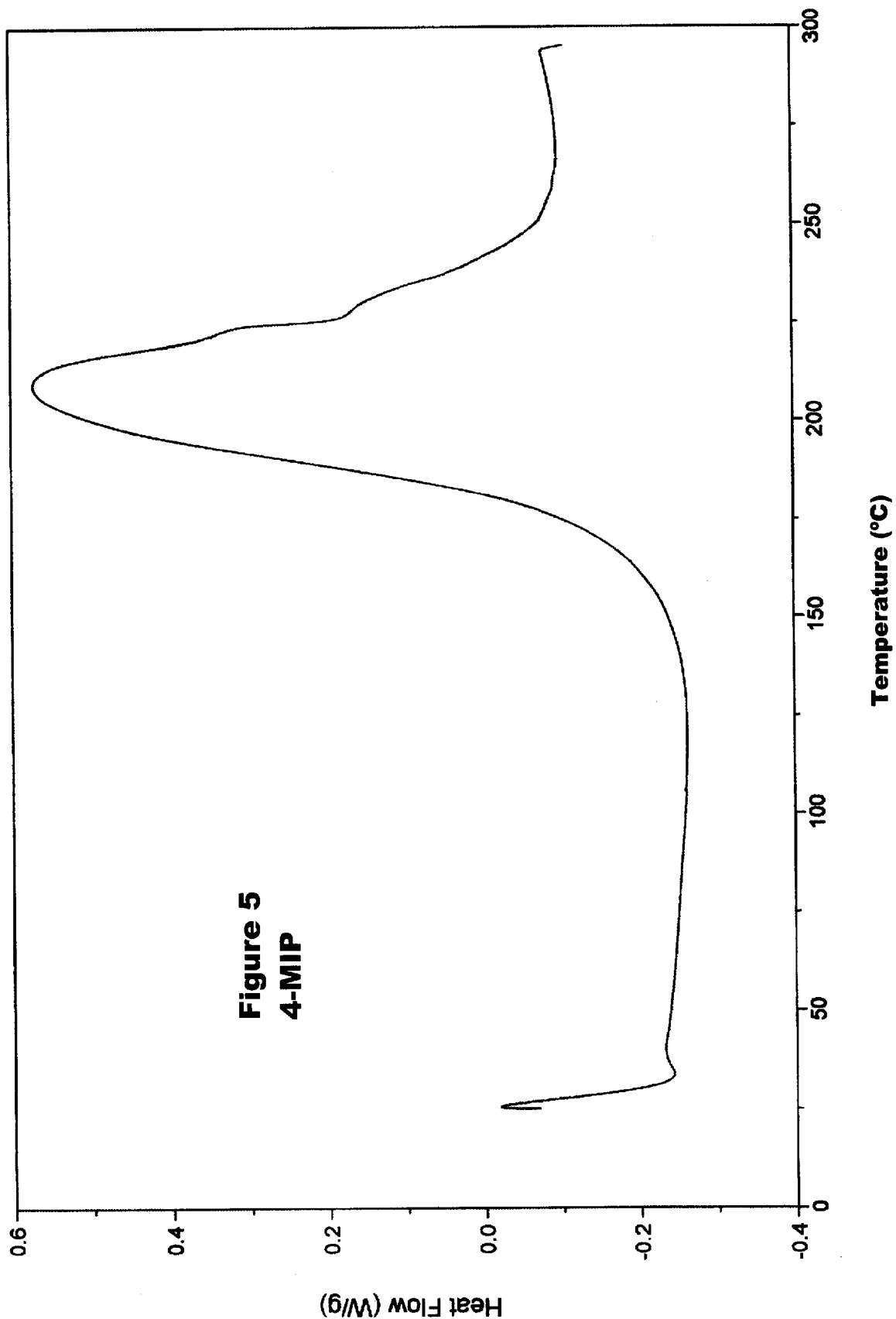
FIG. 5 is the differential scanning calorimetric graph of 4-methylimidazole phosphate as an accelerator in the anhydride cured epoxy composition of Example 12.
Figure 6:
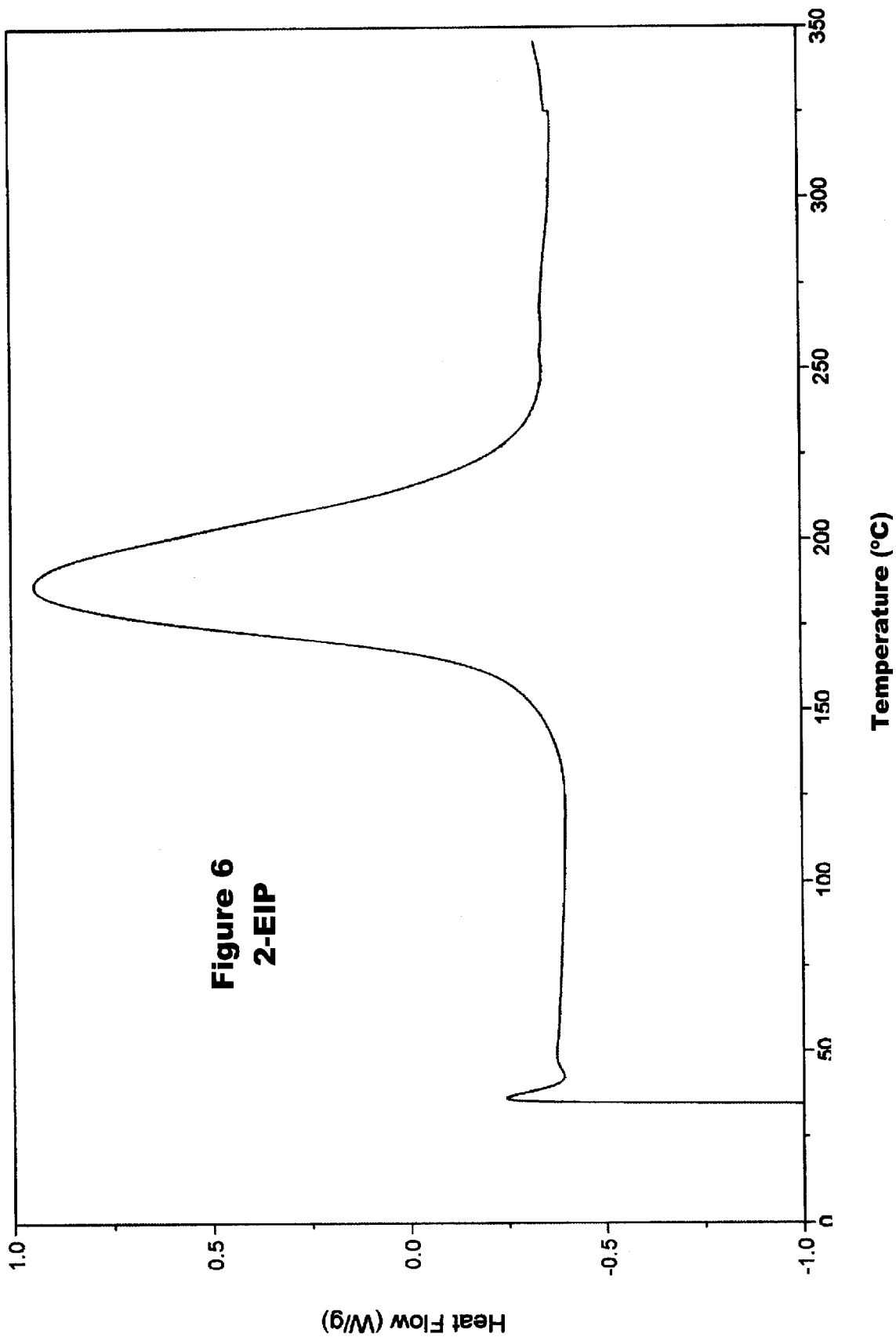
FIG. 6 is the differential scanning calorimetric graph of 2-ethylimidazole phosphate as an accelerator in the anhydride cured epoxy composition of Example 13.

The compositions were tested by DSC to determine the onset temperature of reaction and the peak or maximum temperature attained. Between 5 and 10 mg of the Examples 8–14 compositions were placed on a DSC pan and hermetically sealed. The DSC was run from room temperature to 350° C. at a heating rate of 10° C./min. The difference between the onset temperature ($T_o$) and peak temperature ($T_p$) is a measure of the breadth or speed of the reaction once it has begun. The smaller the difference between onset and peak, the faster and more desirable the cure will be at or near the onset temperature. The data in Table 2 and FIGS. 1–7 clearly show that the 2-PIP accelerator manifested a surprisingly small ($T_p$—$T_o$), i.e., an unexpectedly fast cure, at the onset temperature compared to the other imidazole phosphates.

TABLE 2

| Example | $T_o$ (° C.) | $T_p$ (° C.) | ($T_p$ - $T_o$) (° C.) |
|---|---|---|---|
| 8 (2-PIP) | 179 | 193 | 14 |
| 9 (1-MIP) | 174 | 223 | 49 |
| 10 (2-MIP) | 165 | 208 | 43 |
| 11 (IMP) | 171 | 214 | 43 |
| 12 (4-MIP) | 176 | 209 | 33 |
| 13 (2-EIP) | 162 | 186 | 24 |
| 14 (24-EMIP) | 164 | 203 | 39 |

The phosphoric acid salt of 2-phenylimidazole can be used as a cure accelerator for acid anhydrides in 100% solids epoxy compositions such as epoxy adhesives, coatings including powder coatings, filament winding, printed circuit board and like applications. The salt does not dissociate until it is exposed to elevated temperatures. Therefore, the salt provides good shelf stability in 100% solids one-component epoxy compositions.

STATEMENT OF INDUSTRIAL APPLICATION

The invention provides 2-phenylimidazole phosphate salt as an accelerator for acid anhydride curing agents in one-component 100% solids epoxy compositions.

We claim:

1. In a heat curable one-component epoxy composition comprising an epoxy resin, acid anhydride latent heat activated curing agent and an accelerator for the acid anhydride curing agent, the improvement which comprises a phosphate salt of 2-phenylimidazole as the accelerator.

2. The epoxy composition of claim 1 in which the 2-phenylimidazole phosphate salt comprises a compound the following structure:

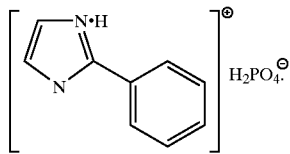

3. The epoxy composition of claim 1 in which the 2-phenylimidazole phosphate salt is prepared by reacting 2-phenylimidazole and phosphoric acid in a 0.9 to 1.1 molar ratio.

4. The epoxy composition of claim 1 in which the 2-phenylimidazole phosphate salt is prepared by reacting 2-phenylimidazole and phosphoric acid in a 1:1 molar ratio.

5. The epoxy composition of claim 1 which the acid anhydride is an aliphatic, cycloaliphatic, aromatic monoanhydride or dianhydride.

6. The epoxy composition of claim 1 in which the acid anhydride is methyl-bicyclo[2,2,1]heptene-2,3-dicarboxylic an hydride isomers tetrahydrophthalic anhydride, methyltetrahydrophthalic anhydride, hexahydrophthalic anhydride or methylhexahydrophthalic anhydride.

7. The epoxy composition of claim 6 in which the 2-phenylimidazole phosphate salt comprises the dihydrogen phosphate salt.

8. The epoxy composition of claim 1 in which the epoxy resin is a diglycidyl ether of bisphenol-A, an advanced diglycidyl ether of bisphenol-A, a diglycidyl ether of bisphenol-F, or an epoxy novolac resin.

9. The epoxy composition of claim 1 in which the epoxy resin is diglycidyl ether of bisphenol-A or diglycidyl ether of bisphenol-F.

10. The epoxy composition of claim 8 in which the acid anhydride is hexahydrophthalic anhydride or methyl hexahydrophthalic anhydride.

11. The epoxy composition of claim 10 in which the 2-phenylimidazole phosphate salt comprises the dihydrogen phosphate salt.

12. The epoxy composition of claim 1 in which the 2-phenylimidazole phosphate salt is present at 0.05 pbw per 100 pbw epoxy resin.

13. A heat curable one-component epoxy composition comprising diglycidyl ether of bisphenol-A or diglycidyl ether of bisphenol-F, hexahydrophthalic anhydride or methylhexahydrophthalic anhydride latent heat activated curing agent, and a phosphate salt of 2-phenylimidazole as an accelerator for the anhydride curing agent.

14. The epoxy composition of claim 13 in which the 2-phenylimidazole phosphate salt comprises a compound the following structure:

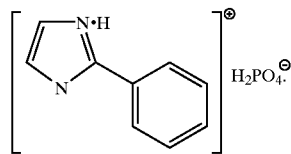

15. The epoxy composition of claim 13 in which the 2-phenylimidazole phosphate salt is prepared by reacting 2-phenylimidazole and phosphoric acid in a 0.9 to 1.1 molar ratio.

16. The epoxy composition of claim 13 in which the 2-phenylimidazole phosphate salt is prepared by reacting 2-phenylimidazole and phosphoric acid in a 1:1 molar ratio.

17. A heat curable one-component epoxy composition comprising 100 pbw epoxy resin which is a diglycidyl ether of bisphenol-A or a diglycidyl ether of bisphenol-F, 75 to 90 pbw latent heat activated curing agent which is hexahydrophthalic anhydride or methylhexahydrophthalic anhydride, and 0.05 to 10 pbw phosphate salt of 2-phenylimidazole.

18. The epoxy composition of claim 17 in which the epoxy resin is diglycidyl ether of bisphenol-A and the latent heat activated curing agent is methylhexahydrophthalic anhydride.

19. The dihydrogen phosphate salt of 2-phenylimidazole.

* * * * *